United States Patent
Roberts (10) Patent No.: US 9,364,148 B2
(45) Date of Patent: Jun. 14, 2016

(54) METHOD AND APPARATUS FOR MEASURING THE DEFORMATION CHARACTERISTICS OF AN OBJECT

(75) Inventor: Cynthia J. Roberts, Columbus, OH (US)

(73) Assignee: CRS & Associates, Columbus, OH (US)

(*) Notice: Subject to any disclaimer, the term of this patent is extended or adjusted under 35 U.S.C. 154(b) by 1687 days.

(21) Appl. No.: 12/091,307

(22) PCT Filed: Oct. 31, 2006

(86) PCT No.: PCT/US2006/060381
§ 371 (c)(1),
(2), (4) Date: Apr. 24, 2008

(87) PCT Pub. No.: WO2007/053826
PCT Pub. Date: May 10, 2007

(65) Prior Publication Data
US 2008/0259276 A1 Oct. 23, 2008

Related U.S. Application Data

(60) Provisional application No. 60/731,756, filed on Oct. 31, 2005.

(51) Int. Cl.
*A61B 3/10* (2006.01)
*A61B 3/16* (2006.01)
(Continued)

(52) U.S. Cl.
CPC .............. *A61B 3/165* (2013.01); *A61B 3/0008* (2013.01); *A61B 3/107* (2013.01)

(58) Field of Classification Search
CPC ....... A61B 3/0008; A61B 3/107; A61B 3/165
USPC .......... 351/205, 210, 212, 247, 221; 600/401, 600/405
See application file for complete search history.

(56) References Cited

U.S. PATENT DOCUMENTS

| 4,621,644 A | 11/1986 | Eilers |
| 4,812,448 A | 3/1989 | Knepper |

(Continued)

OTHER PUBLICATIONS

Grabner et al.; Dynamic Corneal Imaging; J Cataract Refract Surg 2005; vol. 31: 163-174; 2005 ASCRS and ESCRS; Elsevier Inc.
(Continued)

*Primary Examiner* — Huy K Mai
(74) *Attorney, Agent, or Firm* — William Greener; Bond, Schoeneck & King, PLLC (57) ABSTRACT

Embodiments of the invention are generally directed to apparatus and methods for measuring a deformation characteristic of a deformable target surface. The measurement principles of the invention may be applied to a large variety of organic (e.g., human, animal or plant tissue) and inorganic materials having a surface that can be deformed by an applied non-contact force. The surface may be light diffusing and non-transparent or non-diffusing and transparent. An illustrative embodiment of the invention is directed to a device for measuring a deformation characteristic of a cornea. The device comprises a corneal topographer and a non-contact tonometer that is operationally integrated with the corneal topographer. In an aspect, the corneal topographer is a rasterstereography-based topographer. Use of the inventive device enables a method for measuring a deformation characteristic of the cornea. In addition to the measurable deformation characteristics listed above, dioptric power, intraocular pressure, corneal hysteresis, corneal elasticity, corneal viscosity and various known corneal topography characteristics can be measured.

21 Claims, 7 Drawing Sheets

(51) Int. Cl.
*A61B 3/00* (2006.01)
*A61B 3/107* (2006.01)

(56) References Cited

U.S. PATENT DOCUMENTS

| | | | |
|---|---|---|---|
| 4,995,716 A * | 2/1991 | Warnicki et al. | 351/212 |
| 5,131,739 A | 7/1992 | Katsuragi | |
| 5,159,361 A | 10/1992 | Cambier et al. | |
| 5,279,300 A * | 1/1994 | Miwa et al. | 600/401 |
| 6,042,544 A | 3/2000 | Miwa et al. | |
| 6,045,503 A | 4/2000 | Grabner et al. | |
| 6,149,609 A | 11/2000 | Lieberman et al. | |
| 6,379,008 B1 * | 4/2002 | Chateau et al. | 351/247 |
| 6,875,175 B2 * | 4/2005 | Luce | 600/398 |
| 7,425,067 B2 * | 9/2008 | Warden et al. | 351/205 |
| 7,798,962 B2 * | 9/2010 | Luce | 600/405 |
| 7,871,378 B1 * | 1/2011 | Chou et al. | 600/398 |
| 2006/0241367 A1 | 10/2006 | Koest | |
| 2007/0097317 A1 | 5/2007 | Hsyashi et al. | |
| 2008/0259276 A1 | 10/2008 | Roberts | |

OTHER PUBLICATIONS

Edmund, C.; Corneal Topography and Elasticity in Normal and Keratoconic Eyes. A Methodological Study Concerning the Pathogenesis of Keratoconus; Acta Ophthalmol Suppl. 1989; vol. 193; Abstract.

* cited by examiner

METHOD AND APPARATUS FOR MEASURING THE DEFORMATION CHARACTERISTICS OF AN OBJECT

CROSS-REFERENCE TO RELATED APPLICATIONS

This application claims priority to U.S. Provisional Application Ser. No. 60/731,756 filed on Oct. 31, 2005.

BACKGROUND OF THE INVENTION

1. Field of the Invention

Embodiments of the invention generally relate to methods and apparatus for measuring characteristics of a deformable object through changes in the surface of the object during a deformation interval. More particularly, embodiments of the invention relate to the measurement of physical and biomechanical characteristics of a live cornea.

2. Description of Related Art

The measurement of the surface characteristics of an object can reveal much information about the physical and mechanical properties of the object. If the surface of the object is deformable in response to an applied force, measurement of the changes in characteristics of the surface may provide further useful information. There exists numerous organic and inorganic objects having deformable surfaces whose measurement may be of interest in various fields. A particularly interesting, exemplary object is the cornea of a human eye. The widespread interest in understanding the physical, biomechanical, optical and all other characteristics of the eye is obviously motivated. Over the years, different theories have been presented about the structural and dynamic properties of the eye, particularly the cornea. Earlier theories modeling the cornea as a solid structure have more recently given way to understanding the cornea as a layered, biodynamically responsive structure that to this day is not completely understood.

Increased understanding of the structure of the cornea and its interaction with other components of the eye has been achieved by measuring various topographical characteristics of the cornea. These topographical characteristics include corneal curvature and surface elevation with respect to a reference surface, as well as others known in the art. Corneal topography measuring devices are alternatively referred to as topographers, keratographers or keratometers (a topographer is a generic term referring to an apparatus for measuring the topographical characteristics of an object surface, while keratographer and keratometer more specifically refer to measurements of the cornea). Different devices use different measuring principles to determine various topographical characteristics of the cornea. For example, some devices use Placido-based reflective image analysis. Placido-based devices can measure curvature parameters of the cornea but typically lack the capability to directly measure surface elevation. The Orbscan® anterior segment analyzer (Bausch & Lomb Incorporated) is a topography characteristic measuring device that utilizes a scanning optical slit. Device software provides for direct measurement of surface elevation and corneal thickness as well as surface curvature. Another commercial device developed by Par Technology Corporation is known as the PAR CTS™ Corneal Topography System (PAR). The PAR imaging system utilizes a raster photography method. The PAR CTS imaging system projects a known grid geometry onto the anterior corneal surface that is viewed by a camera from an offset axis. Other topography characteristic measuring techniques include confocal microscopy, optical coherence tomography, ultrasound, optical interferometry and others, all of which are well known in the art.

While the measurement of various topographical characteristics of the cornea provide a wealth of information about vision and the effects of corneal shape on visual performance, corneal topography by itself cannot reveal the physical and biomechanical properties of the cornea necessary for a thorough understanding of its structure and function. In order to better understand the biomechanical and biodynamic properties of the cornea, it is necessary to know something about the elastic and viscoelastic properties of the cornea. One technique used to explore these properties is to deform the cornea with a known force and measure the response of the cornea to the force. An illustrative apparatus of this type is known in the art as a tonometer. Tonometers for measuring intraocular pressure (IOP) where originally developed as contact-type instruments, meaning that a portion of the instrument is brought into contact with the cornea during the measurement procedure. A well known instrument of this type is the Goldmann applanation tonometer (GAT) originally developed in the 1950s. The GAT measures the force required to flatten ("applanate") a known area of the cornea, and is used today as a standard against which other types of tonometers are compared to assess measurement accuracy.

Patient discomfort caused by contact tonometers such as the GAT led to the development of "non-contact" tonometers, which operate by directing an air pulse generated by a pump mechanism through a discharge tube aimed at the cornea to cause applanation. As the cornea is deformed by the fluid pulse, an optoelectronic system monitors the cornea by detecting corneally reflected light from a beam obliquely incident upon the cornea. A peak detector signal occurs at the moment of applanation when the reflecting surface of the cornea is flat. During a non-contact IOP measurement, the cornea is actually deformed from its original convex state through a first state of applanation to a slightly concave state and is allowed to return from concavity through a second state of applanation to convexity as the air pulse decays.

A method for measuring IOP and a non-contact tonometer are disclosed in U.S. Pat. Nos. 6,419,631 and 6,875,175, the disclosures of which are hereby incorporated by reference in their entireties to the fullest extent allowed by applicable laws and rules. This technology is commercially known as the Reichert (Depew, New York) Ocular Response Analyzer™. According to posted information accessible at http://ocular-response.reichertoi.com, the Reichert Ocular Response Analyzer utilizes a dynamic bidirectional applanation process to measure a cornea tissue property called corneal hysteresis. The term corneal hysteresis refers to the difference in pressure values of the air pulse at the inward moving applanation point and the outward moving applanation point during a measurement interval (inward moving refers to an initial convex corneal shape moving to a flattened condition, while the outward applanation point refers to the post air pulse concave corneal surface moving towards the applanation point on its return to a normal convex surface shape). Since corneal hysteresis appears to be a repeatable measurement, it may provide a metric that is useful for identifying and categorizing various conditions of the cornea. For example, measurement of corneal hysteresis is alleged to aid in identifying and classifying conditions such as corneal ectasia and Fuch's Dystrophy, and as helping in the diagnosis and management of glaucoma. Differences in hysteresis measurements for different corneal conditions may better inform about the biomechanical and biodynamical properties of the cornea. Because corneal hysteresis measurement is credited for presenting a complete characterization of the cornea's biomechanical state, it is believed to have additional potential uses in screening refractive surgery candidates as well as predicting and controlling surgical outcomes. The interested reader is directed to the aforementioned website address for further information provided by the manufacturer.

In view of the foregoing described techniques, capabilities and apparatus for measuring corneal parameters such as topography characteristics and hysteresis, for example, the inventor has recognized that additional benefits could be obtained by a combination of the techniques and integration of the different apparatus. The inventor has further recognized the need for new and improved methods and apparatus that are capable of more efficiently measuring properties of the cornea, resulting in a better understanding of corneal biomechanics and biodynamics.

SUMMARY OF THE INVENTION

Embodiments of the invention are generally directed to apparatus and methods for measuring a deformation characteristic of a deformable target surface. It is to be understood that the measurement principles of the invention may be applied to a large variety of organic (e.g., human, animal or plant tissue) and inorganic materials having a surface that can be deformed by an applied non-contact force. The surface may be light diffusing and non-transparent or non-diffusing and transparent. Apparatus suitable for measuring the surface topography characteristics of a deformable target surface during or over (i.e., throughout) a deformation interval, that incorporate a component which can supply a non-contact force that deforms the target surface over the deformation interval, are considered to be within the scope of the claimed invention. As such, an embodiment of the invention is directed to a device for measuring a deformation characteristic of a deformable target surface that includes a topographer and a non-contact target surface deformer that is operationally integrated with the topographer and is located along a first, central, operational axis of the device. As used throughout this specification, the phrase 'operationally integrated' is defined herein to mean that the deformation force-providing device and the topography characteristic-measuring device operate simultaneously and share optical pathways and time (deformation and measurement) intervals. In other words, each device is dependent upon the other and neither can stand alone for operational functionality according to the embodiments of the invention. Thus the use of the term 'operationally integrated' in the appended claims is limited to the meaning set forth immediately above. According to an aspect, the topographer includes a high speed camera located along a second, operational axis of the device. A suitable camera or detector is required to capture sequential images or still images of specific deformation events during the deformation interval. The device also includes an optical system including a grid object and a light source for projecting a grid image, aligned along a third, operational axis of the device. In a particular aspect, at least one of the second and third axes are offset from the first axis. More particularly, all of the axes are directionally independent.

In a related aspect in which the target object is a live cornea of an eye, the topographer advantageously is a computer-assisted videokeratography-based topographer (referred to herein as a corneal topographer). In a particular aspect, the corneal topographer is a modified PAR CTS imaging device. According to an aspect, the non-contact target surface deformer is an air pressure pulse-based apparatus. In a particular aspect, the non-contact target surface deformer is a non-contact tonometer.

According to a related method embodiment for measuring a deformation characteristic of a deformable target surface, a device including a topographer for making a topography characteristic measurement of the target surface and a non-contact force producing component apparatus is provided. The target surface to be measured is suitably positioned with respect to the device. The target surface is subjected to the force and experiences responsive deformation over a deformation interval. A plurality of in-vivo topography characteristic measurements are made during the deformation interval. Exemplary topography characteristic measurements may include, but are not limited to, surface curvature, surface elevation, surface indentation, surface deformation symmetry, surface deformation shape, surface deformation area, surface deformation hysteresis and elasticity, viscosity and pressure.

An illustrative and particularly advantageous embodiment of the invention is directed to a device for measuring a deformation characteristic of a cornea. The device comprises a corneal topographer and a non-contact tonometer that is operationally integrated with the corneal topographer. In a particularly advantageous aspect, the corneal topographer is a rasterstereography-based topographer. More particularly, the corneal topographer is a modified PAR CTS imaging device.

Use of the aforementioned device enables a method for measuring a deformation characteristic of the cornea. In addition to the measurable deformation characteristics listed above, dioptric power, intraocular pressure, corneal hysteresis, corneal elasticity, corneal viscosity and various known corneal topography characteristics can be measured.

Additional features and advantages of the invention will be set forth in the detailed description which follows, and in part will be readily apparent to those skilled in the art from that description or recognized by practicing the invention as described herein, including the claims as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DETAILED DESCRIPTION OF EMBODIMENTS OF THE INVENTION

Figure 1:
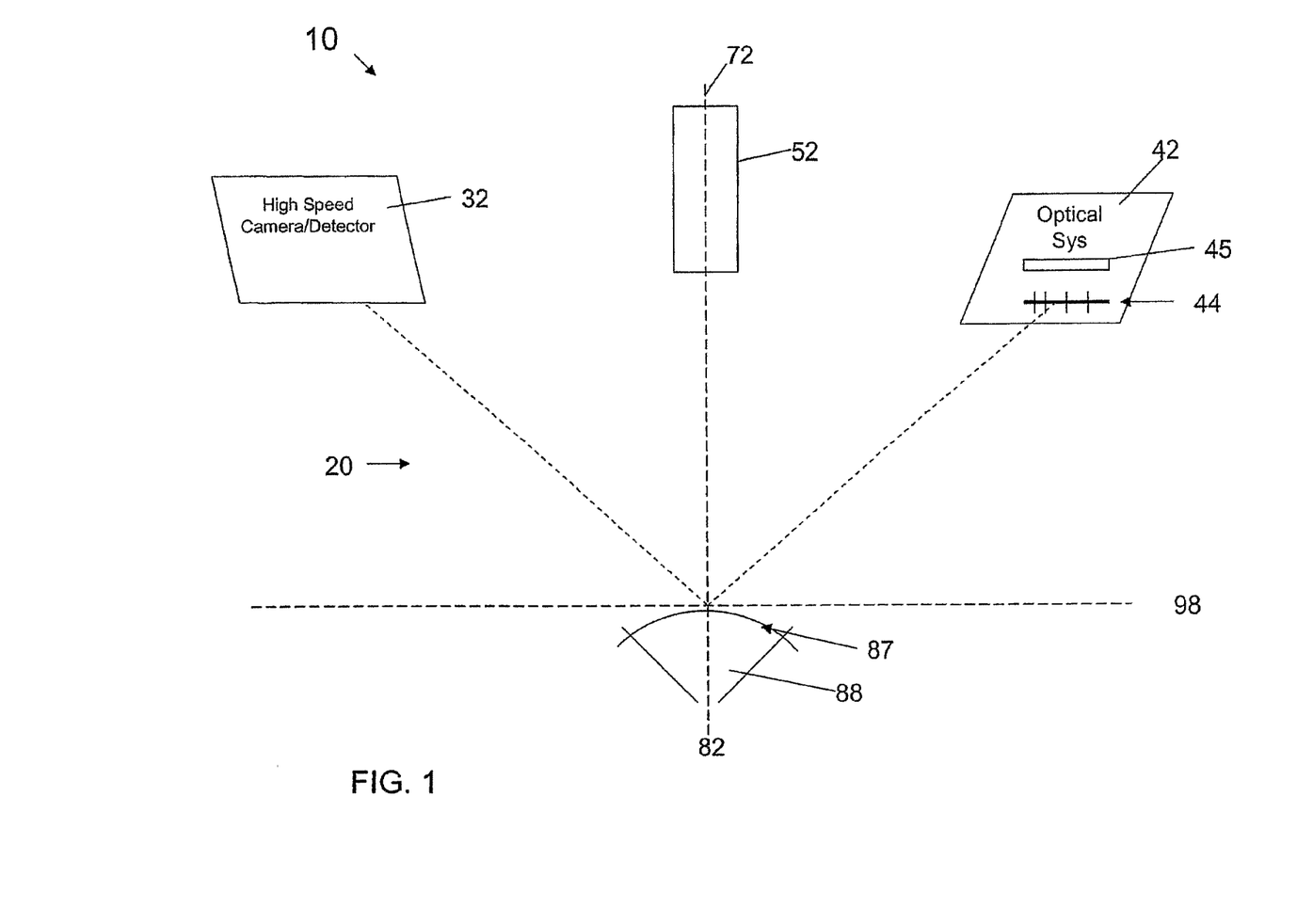
FIG. 1 is a schematic plan view of a device according to an embodiment of the invention.

An embodiment of the invention is generally directed to a device for measuring a deformation characteristic of a deformable target surface. An exemplary embodiment of the invention is directed to a device 10, as shown in FIG. 1, for measuring a deformation characteristic of a live cornea. Wherever possible, the same reference numbers will be used throughout the drawings to refer to the same or like parts. The device 10 includes a corneal topographer 20 and a non-contact tonometer 30 that are operationally and physically integrated components of the device.

The corneal topographer 20 of the device shown in FIG. 1 is a rasterstereography-based topographer that is modeled after a PAR CTS corneal topography system. Such a system is disclosed in U.S. Pat. Nos. 4,995,716 and 5,159,361, the disclosures of which are incorporated herein by reference to the fullest allowable extent as though fully set forth in their entireties. The corneal topographer 20 includes a high speed camera/detector 32 located along a second, operational axis 76 of the device 10 and an optical system 42, including a grid object 44 and a light source 45, for projecting a grid image, aligned along a third, operational axis 78 of the device 10. The target object, in this case the cornea 87 of an eye 88, is located along a central device axis 82 in a measurement plane illustrated by dotted line 98. Various lenses and filters that are components of the PAR CTS corneal topographer 20 are not shown.

Figure 2A:
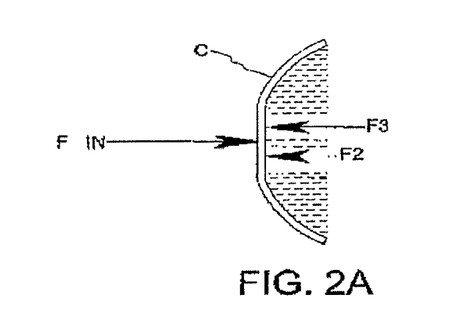
FIG. 2A is a schematic force diagram of a cornea at a first moment of applanation.
Figure 2B:
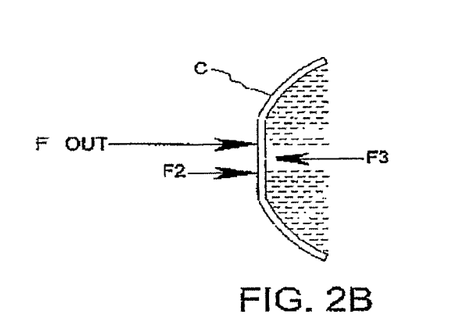
FIG. 2B is a schematic force diagram of a cornea at a second moment of applanation.

The exemplary device 10 also includes a non-contact tonometer 52 located along a first operational axis 72. Axis 72 and axis 82 are coplanar. Second and third operational axes 76, 78 are thus off-set. In an illustrative aspect, non-contact tonometer 52 is a Reichert Ocular Response Analyzer, a description of which is set forth in aforementioned U.S. Pat. Nos. 6,419,631 and 6,875,175. Once the cornea is suitably positioned in the measurement plane 98, measurement begins with generation of a metered air pulse directed at the cornea. The impulse energy imparted to the cornea by the air pulse reversibly deforms the cornea from its original state of convexity through a first state of applanation, $P_1$, to a state of concavity. As the air pulse decays or is controllably diminished by de-energizing the pump solenoid, the cornea returns from concavity back through a second state of applanation, $P_2$, to its original state of convexity. This deformation occurs over a deformation interval T referenced in FIG. 3. FIGS. 2A and 2B are simplified diagrams showing the forces acting on a cornea C at the moment ($t_1$) of first applanation (FIG. 2A) and second ($t_2$) applanation (FIG. 2B) during the measurement interval, while ignoring dynamic effects. In the figures, $F_1$ represents the inwardly directed force of an incident air pulse, $F_2$ represents the force required to bend the corneal tissue itself, and $F_3$ represents the outwardly directed force attributed to intra-ocular pressure.

Figure 3:
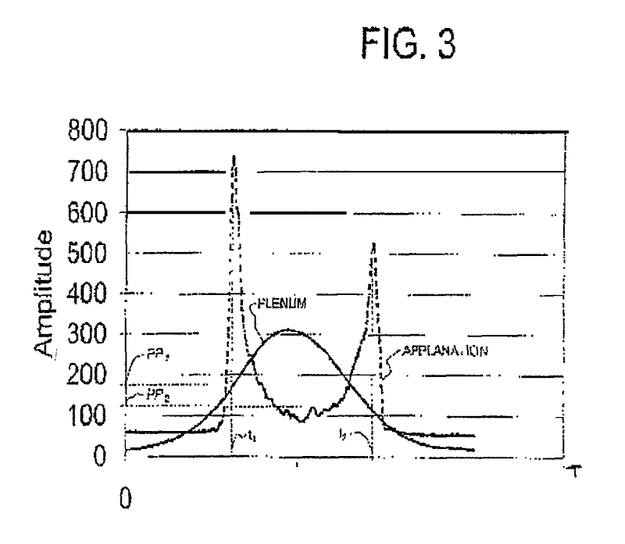
FIG. 3 is a graph showing applanation detection and plenum pressure signals for a deformation characteristic measurement according to an embodiment of the invention.

Based upon the operational principles of the Ocular Response Analyzer, the corneal topographer 20 can conveniently be triggered off of event $P_1$ at time $t_1$, event $P_2$ at time $t_2$, at peak plenum pressure and/or at any predetermined trigger points over the deformation interval T to obtain a plurality of deformation characteristic measurements.

According to the exemplary apparatus embodiment, use of the PAR CTS system modified to incorporate a high speed camera/detector as the corneal topographer 20 in device 10 is advantageous because the off-set axes 76, 78 of the camera 32 and optical system 42 provide for a centralized location of the tonometer 52. Although a Placido-based topographer may not allow the tonometer to be centrally located, other topography characteristic measuring apparatus may provide a suitable physical arrangement to be used in device 10.

Figure 4:
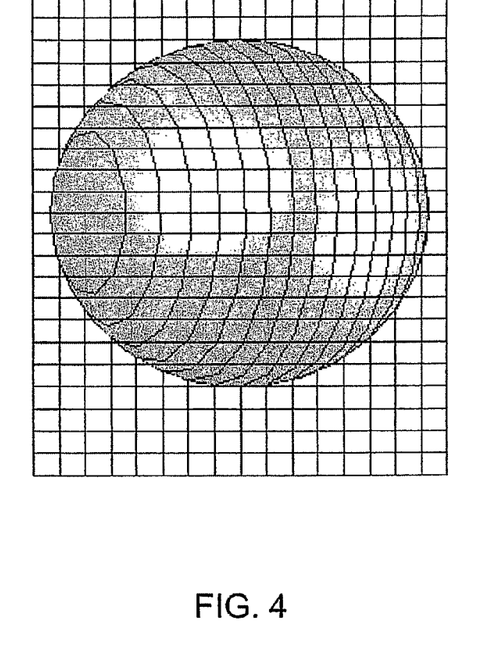
FIG. 4 is a top view of a projected PAR CTS grid on a simulated cornea before air puff deformation of the corneal surface.
Figure 5:
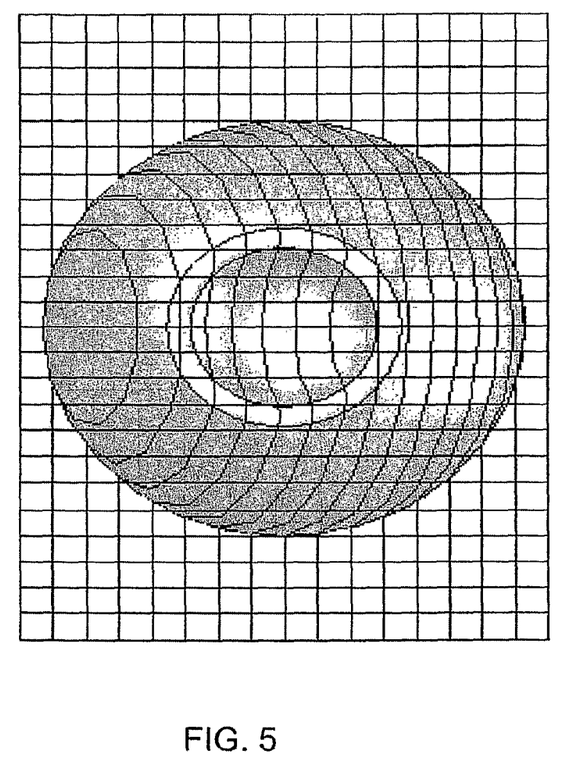
FIG. 5 is a top view of a projected PAR CTS grid on a simulated cornea after an air puff deformation of the corneal surface.
Figure 6:
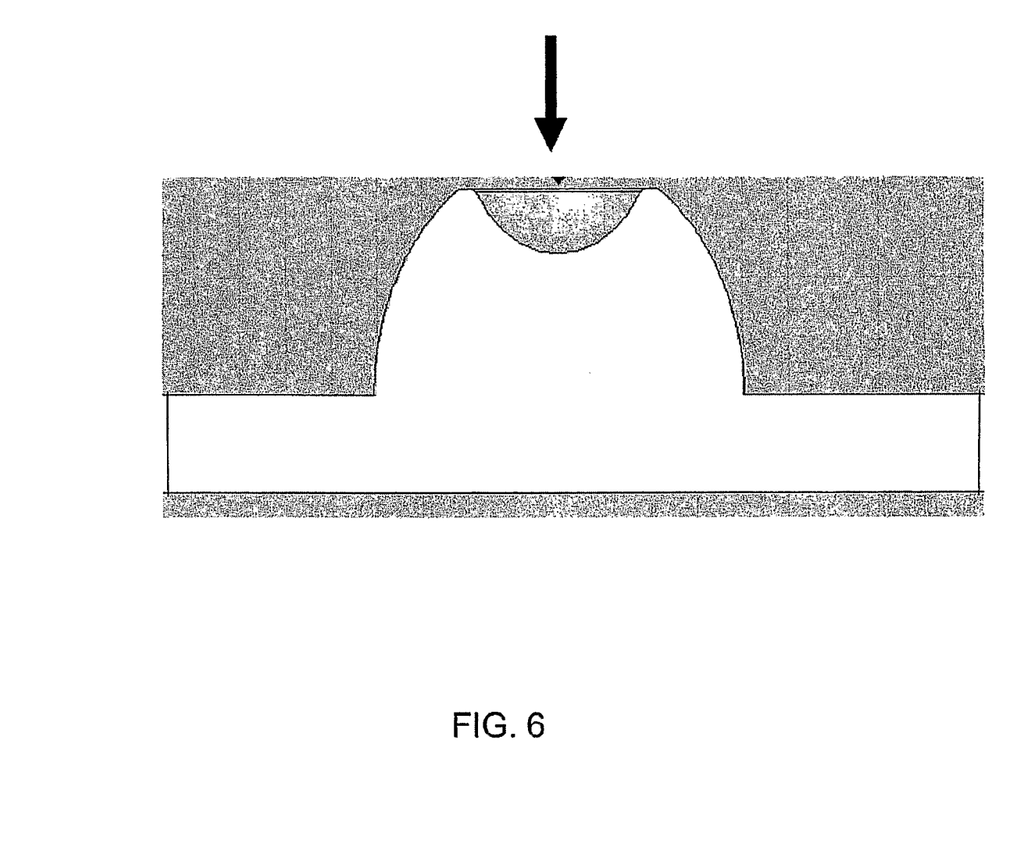
FIG. 6 is a schematic side view of corneal indentation corresponding to the deformation shown in FIG. 5.
Figure 7:
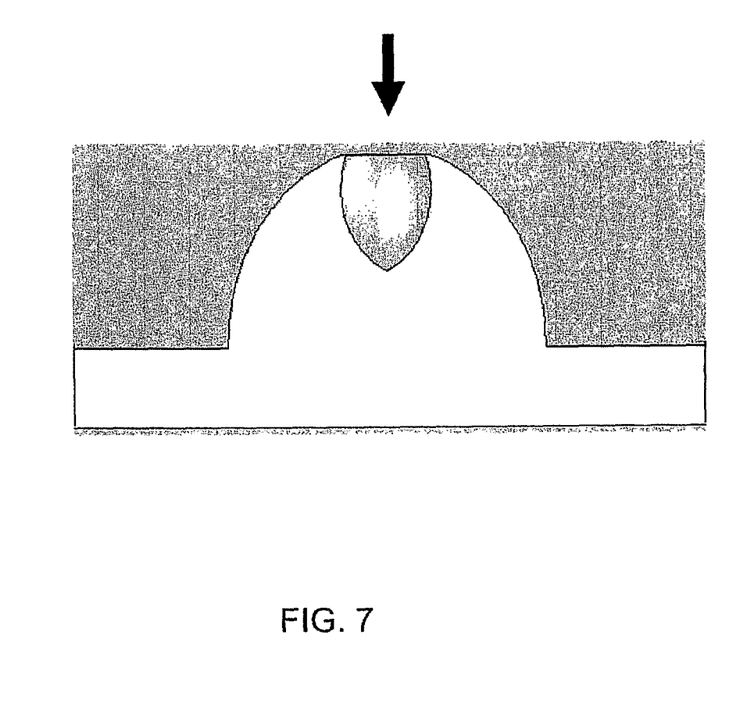
FIG. 7 is a schematic side view of corneal indentation showing a narrower, deeper corneal indentation that that shown in FIG. 6.

FIGS. 4 and 5 show simulated PAR CTS grid images before and after, respectively, an air puff deformation of a corneal surface. FIG. 6 illustrates a wide, shallow corneal indentation corresponding to that in FIG. 5. For comparative illustration, FIG. 7 shows a narrower and deeper corneal indentation than that shown in FIG. 6. The figures illustrate that softer or stiffer corneas may respond differently to an applied deformation force.

Various deformation characteristics can be measured with the device embodiment described above. For example, the magnitude, the symmetry or asymmetry, the shape and the area of the surface deformation could be measured during the deformation interval, as well as applanation depth, corneal curvature, elevation, hysteresis, corneal elasticity and viscosity, and IOP.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

I claim:

1. A device for measuring deformation characteristics of a live cornea throughout a deformation time interval, comprising:
    a corneal topographic characteristic-measuring apparatus, which can measure a topographic deformation characteristic of the live cornea, which includes an optical system disposed along an operational axis, which further includes a spatially-distributed grid object, an image of which is disposable over a substantial portion of the surface of the live cornea; and
    a non-contact, deformation force-providing apparatus disposed along a central operational axis, which can deform the live cornea over the deformation time interval, wherein the corneal topographic characteristic-measuring apparatus and the non-contact, deformation force-providing apparatus are operationally integrated such that the topographic deformation characteristic of the live cornea over the spatially-distributed region of the surface of the cornea covered by the image of the grid can be measured by the corneal topographic characteristic-measuring apparatus during the deformation time interval over which the live cornea is being deformed by the non-contact, deformation force-providing apparatus.

2. The device of claim 1, wherein the corneal topographic characteristic-measuring apparatus includes a high speed camera located along an operational axis of the device.

3. The device of claim 1, wherein the non-contact, deformation force-providing apparatus is an air puff-based tonometer.

4. The device of claim 3, wherein the tonometer provides a metered, collimated air pulse.

5. The device of claim 1, further wherein the non-contact, deformation force-providing apparatus is located along a first, operational axis of the device, further wherein the corneal topographic characteristic-measuring apparatus includes a camera located along a second, operational axis of the device and an optical system including the grid object and a light source for projecting the grid image onto the live cornea, aligned along a third, operational axis of the device, further wherein all of the axes are directionally independent.

6. The device of claim 5, wherein the first, operational axis is intermediate the second and third operational axes.

7. The device of claim 6, wherein the first, operational axis is a central operational axis of the device.

8. The device of claim 1, wherein the corneal topographic characteristic-measuring apparatus is a rasterstereography-based topographer.

9. The device of claim 1, wherein the corneal topographic characteristic-measuring apparatus is a modified PAR CTS imaging device.

10. A method for measuring an in-vivo deformation characteristic of a cornea, comprising:
   providing a device for making a topography characteristic measurement of the cornea;
   positioning the cornea in a suitable measurement position;
   providing a spatially-distributed image of a grid over a substantial portion of the corneal surface;
   providing a non-contact, deformation force-providing apparatus that is operationally integrated with the topography characteristic-measuring device such that a deformation characteristic of the live cornea over the spatially-distributed region of the surface of the cornea covered by the image of the grid is measured by the corneal topographic characteristic-measuring apparatus simultaneously with and during a deformation time interval over which the live cornea is being deformed by the non-contact, deformation force-providing apparatus;
   deforming the cornea over the deformation time interval; and
   making a plurality of the topography characteristic measurements over the spatially-distributed region of the surface of the cornea covered by the image of the grid simultaneously with the deformation of the cornea during the deformation interval.

11. The method of claim 10, comprising providing a symmetrical corneal deformation force.

12. The method of claim 10, comprising providing an air pressure pulse as the corneal deformation force.

13. The method of claim 10, wherein making a plurality of the topography characteristic measurements over the deformation interval comprises triggering the topographer at a selected time or by a selected event over the deformation interval.

14. The method of claim 13, wherein the selected time or event includes at least one of a state of corneal convexity, a first state of applanation, a state of corneal concavity and a second state of applanation.

15. The method of claim 10, further comprising measuring a magnitude of surface indentation during the deformation interval.

16. The method of claim 10, further comprising measuring the symmetry or asymmetry of the target surface during the deformation interval.

17. The method of claim 10, further comprising measuring the surface indentation shape during the deformation interval.

18. The method of claim 10, further comprising measuring the surface indentation area during the deformation interval.

19. The method of claim 10, further comprising determining a measure of hysteresis.

20. The method of claim 10, further comprising determining a measure of corneal elasticity.

21. The method of claim 10, further comprising determining a measure of corneal viscosity.

\* \* \* \* \*